United States Patent
Kellar et al.

(10) Patent No.: US 9,770,279 B2
(45) Date of Patent: Sep. 26, 2017

(54) METHOD AND APPARATUS FOR EXTRACTION OF MEDICAL IMPLANTS

(71) Applicant: Little Engine, LLC, Gastonia, NC (US)

(72) Inventors: Franz W. Kellar, Gastonia, NC (US); Harold L. Crowder, Kannapolis, NC (US); Michael D. Bissette, Belmont, NC (US); Nathan W. Kellar, Belmont, NC (US); Mark S. Wabalas, Huntersville, NC (US)

(73) Assignee: Little Engine, LLC, Gastonia, NC (US)

( * ) Notice: Subject to any disclaimer, the term of this patent is extended or adjusted under 35 U.S.C. 154(b) by 0 days.

(21) Appl. No.: 15/157,928

(22) Filed: May 18, 2016

(65) Prior Publication Data

US 2016/0338751 A1    Nov. 24, 2016

Related U.S. Application Data

(60) Provisional application No. 62/163,121, filed on May 18, 2015.

(51) Int. Cl.
*A61B 17/92* (2006.01)
*A61F 2/46* (2006.01)

(52) U.S. Cl.
CPC .......... *A61B 17/921* (2013.01); *A61F 2/4607* (2013.01); *A61F 2/4609* (2013.01); *A61B 2017/924* (2013.01); *A61F 2002/4619* (2013.01); *A61F 2002/4628* (2013.01)

(58) Field of Classification Search
CPC ............... A61N 7/00; A61F 2002/4683; A61F 2002/4619; A61F 2002/4632; A61F 2002/4631; A61F 2/4607; A61B 17/8847
USPC .......................................................... 606/99
See application file for complete search history.

(56) References Cited

U.S. PATENT DOCUMENTS

| | | | | |
|---|---|---|---|---|
| 4,248,232 A | * | 2/1981 | Engelbrecht | A61N 7/00 156/754 |
| 5,019,083 A | * | 5/1991 | Klapper | F16L 37/2445 606/86 R |
| 5,045,054 A | * | 9/1991 | Hood | A61B 17/8847 604/22 |
| 5,318,570 A | | 6/1994 | Hood et al. | |
| 5,324,297 A | | 6/1994 | Hood et al. | |
| 5,330,481 A | | 7/1994 | Hood et al. | |
| 5,382,251 A | * | 1/1995 | Hood | F16L 37/2445 606/2 |
| 5,456,686 A | | 10/1995 | Klapper et al. | |

(Continued)

OTHER PUBLICATIONS

Sukhikh,A. , International Search Report and Written Opinion for PCT/US2016/033085, Sep. 22, 2016, Moscow, Russia.

*Primary Examiner* — David Bates
(74) *Attorney, Agent, or Firm* — Trego, Hines & Ladenheim, PLLC

(57) ABSTRACT

An apparatus for extracting a medical implant from bone includes: a housing; a coupler carried by the housing and configured to be mechanically connected to a medical implant; and a forcing mechanism carried by the housing and operable to apply a cyclic excitation force with a specified amplitude, frequency, and vector to the coupler. Methods are described for using the apparatus to remove and/or implant medical implants.

13 Claims, 25 Drawing Sheets

(56) References Cited

U.S. PATENT DOCUMENTS

| | | | |
|---|---|---|---|
| 5,536,272 A * | 7/1996 | Young | A61B 17/8847 606/99 |
| 5,662,122 A | 9/1997 | Evans | |
| 5,885,299 A | 3/1999 | Winslow et al. | |
| 5,885,301 A * | 3/1999 | Young | A61B 17/8847 606/86 R |
| 6,683,280 B1 * | 1/2004 | Wofford | A61B 17/8802 219/233 |
| 6,932,308 B2 | 8/2005 | Talish et al. | |
| 7,335,205 B2 | 2/2008 | Aeschlimann et al. | |
| 8,128,626 B2 * | 3/2012 | Justin | A61B 17/7044 606/62 |
| 8,292,895 B2 | 10/2012 | Bubb | |
| 8,419,640 B1 * | 4/2013 | Saha | A61B 17/8847 600/437 |
| 8,911,234 B2 | 12/2014 | Mayer et al. | |
| 9,198,776 B2 * | 12/2015 | Young | A61F 2/4607 |
| 2002/0143268 A1 | 10/2002 | Meredith et al. | |
| 2003/0078586 A1 | 4/2003 | Shapira | |
| 2005/0119666 A1 * | 6/2005 | Bubb | A61B 17/8847 606/99 |
| 2005/0240197 A1 | 10/2005 | Kmiec | |
| 2016/0192975 A1 * | 7/2016 | Winnen | A61C 8/005 433/173 |

\* cited by examiner

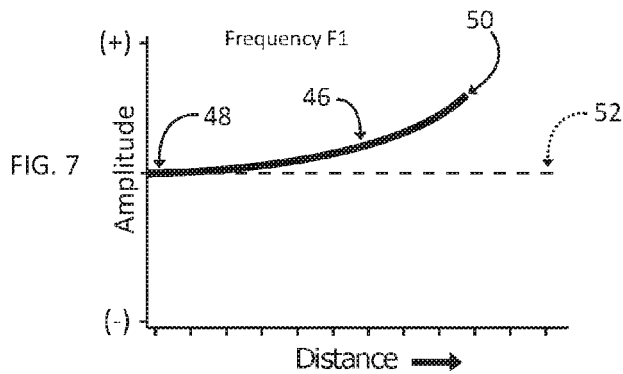
FIG. 7
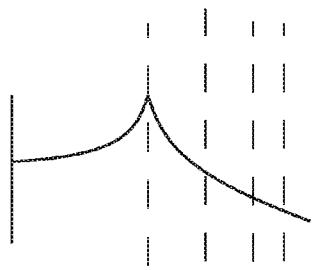
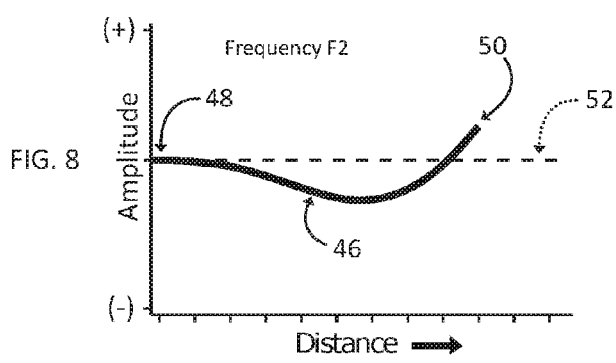
FIG. 8
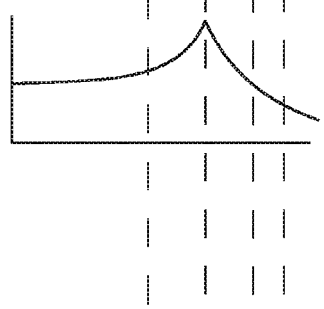
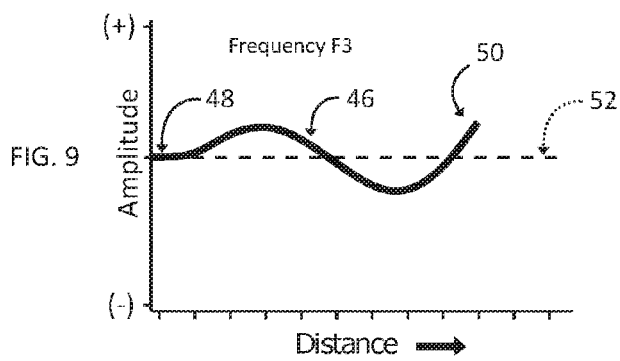
FIG. 9
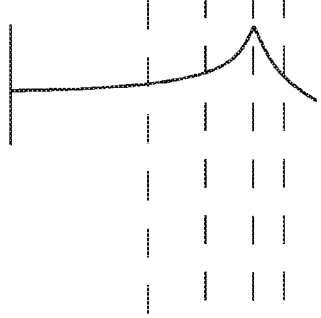
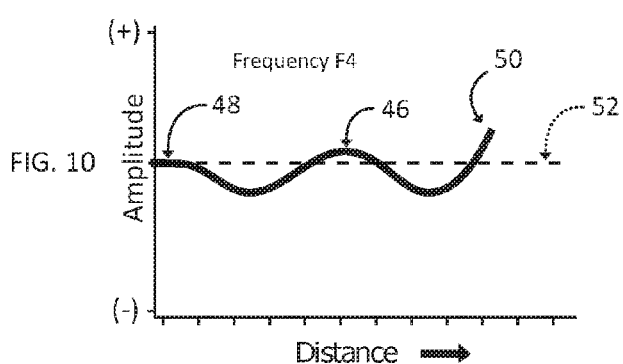
FIG. 10
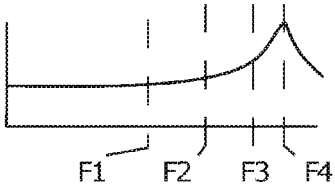

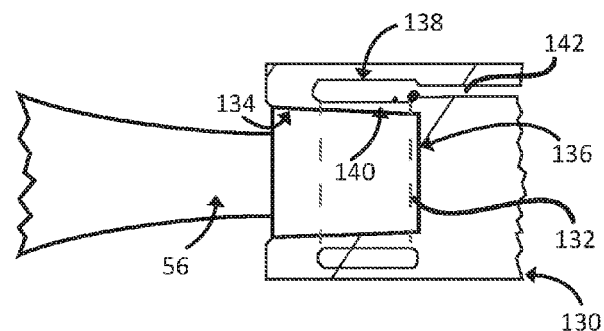
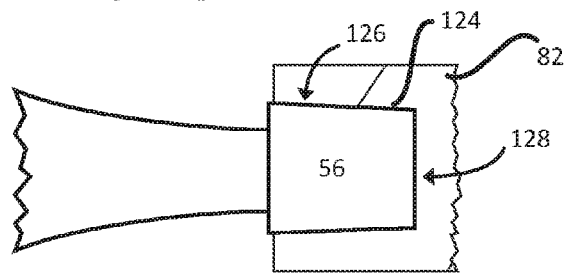
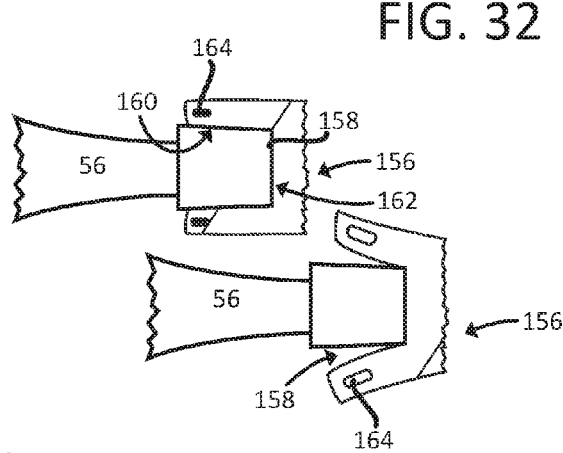
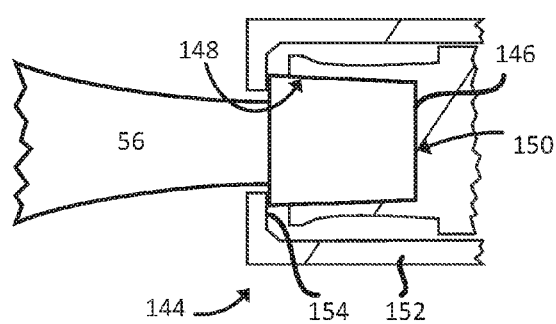

METHOD AND APPARATUS FOR EXTRACTION OF MEDICAL IMPLANTS

BACKGROUND OF THE INVENTION

This invention relates generally to medical implants, and more particularly to methods and apparatus for removing medical implants.

Medical implants, such as knee, hip, shoulder, and spine orthopedic replacement joints and other joints and implants typically comprise one or more bone-implantable elements connected to one or more articulating elements. Other implants such as intramedullary rods, screws and plates also have bone integration features. The bone-implantable elements are implanted into the bones of the joint, and the articulating elements, when present, bear against each other to transfer loads between the bones while permitting appropriate movement (e.g. ball-and-socket, hinge, and/or sliding action).

For example, FIG. 1 illustrates a typical implant 10 in a human body. More specifically, the implant 10 is a hip endoprosthesis comprising a cup 12 implanted into the acetabulum 14 of a pelvis 16 and carrying a hemispherical liner 18, and a stem 20 implanted into the canal 22 of the femur 24, from which the native femoral head has been removed. The stem 20 carries a ball 26 which articulates against the liner 18.

Post-implantation, a bond interface 28 is present between the stem 20 and the surrounding bone "B". Depending on the specific implantation method, the bond interface 28 could be metal-to-bone, metal-to-cement-to bone, metal-to-oxidation layer-to-bone (especially when titanium is the implant substrate), or metal-to-coating-to-bone.

For various reasons such as wear, damage, or a desire to substitute a newer implant design, it is often desirable to remove or extract an implant. However, the pull-out force is significant because the bond interface 28 extends over a large surface area. In the prior art, extraction often requires brute-force mechanical extraction tools, such as the slide hammer 30 shown in FIG. 2, optionally combined with cutting or chiseling cement and/or bone away from the implant perimeter. This method consumes significant amounts of valuable time of the surgeon and hospital. It also subjects the patient (who is often elderly) to long times under anesthesia with attendant risk, and it can cause significant trauma to the bone and surrounding structures.

Accordingly, there is a need for an apparatus and method to extract implants quickly without excessive effort or damage.

BRIEF SUMMARY OF THE INVENTION

This need is addressed by the present invention, which provides a method and apparatus for removing an implant by using targeted and managed harmonics to break the bond interface.

BRIEF DESCRIPTION OF THE DRAWINGS

The invention may be best understood by reference to the following description taken in conjunction with the accompanying drawing figures in which:

FIG. 7 is a graph illustrating a first mode shape of a generalized cantilevered beam in response to an applied cyclic excitation force;

FIG. 8 is a graph illustrating a second mode shape of a generalized cantilevered beam in response to an applied cyclic excitation force;

FIG. 9 is a graph illustrating a third mode shape of a generalized cantilevered beam in response to an applied cyclic excitation force;

FIG. 10 is a graph illustrating a fourth mode shape of a generalized cantilevered beam in response to an applied cyclic excitation force;

FIG. 29 is a schematic, cross-sectional view of a coupler;
FIG. 30 is a schematic, cross-sectional view of a coupler;
FIG. 31 is a schematic, cross-sectional view of a coupler;
FIG. 32 is a schematic, cross-sectional view of a coupler in a closed condition;
FIG. 33 is a schematic, cross-sectional view of a coupler in an open condition;

DETAILED DESCRIPTION OF THE INVENTION

In general, the present invention provides apparatus and methods to break the bond interface 28 above sufficiently that the implant 10 can be removed using only moderate, nominal force.

The method described herein can be used with any type of bone-implanted device. Non-limiting examples of bone-implanted devices include osteoprostheses such as hip, shoulder, and knee joints, intramedullary rods or nails, and bone screws.

The method described herein can also be used with various types of bond interfaces. Examples of common bond interfaces used with medical implants are shown in FIGS. 3-5.

Figure 1:
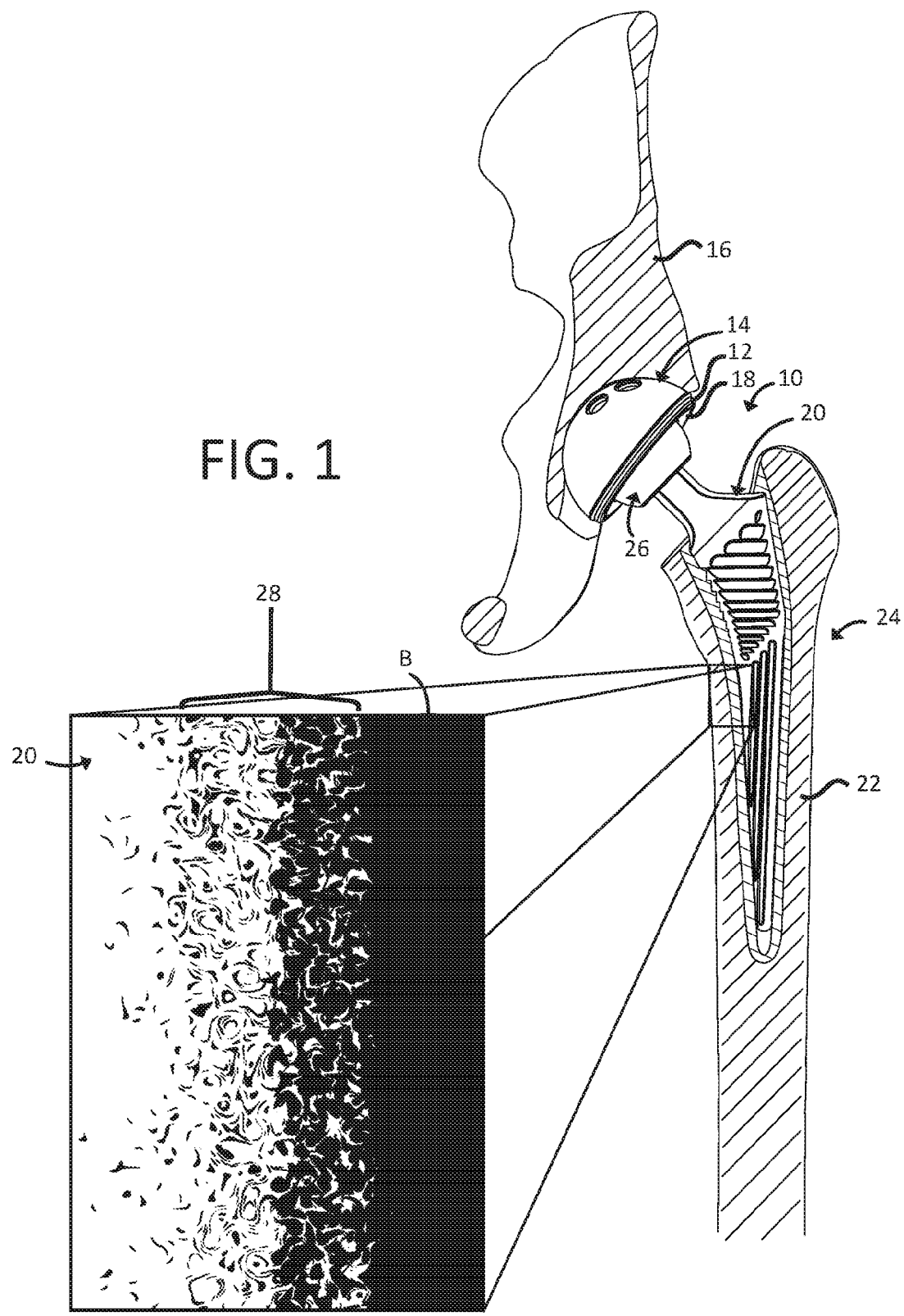
FIG. 1 is cross-sectional view of a human pelvis and femur with a hip prosthesis implanted therein.
Figure 2:
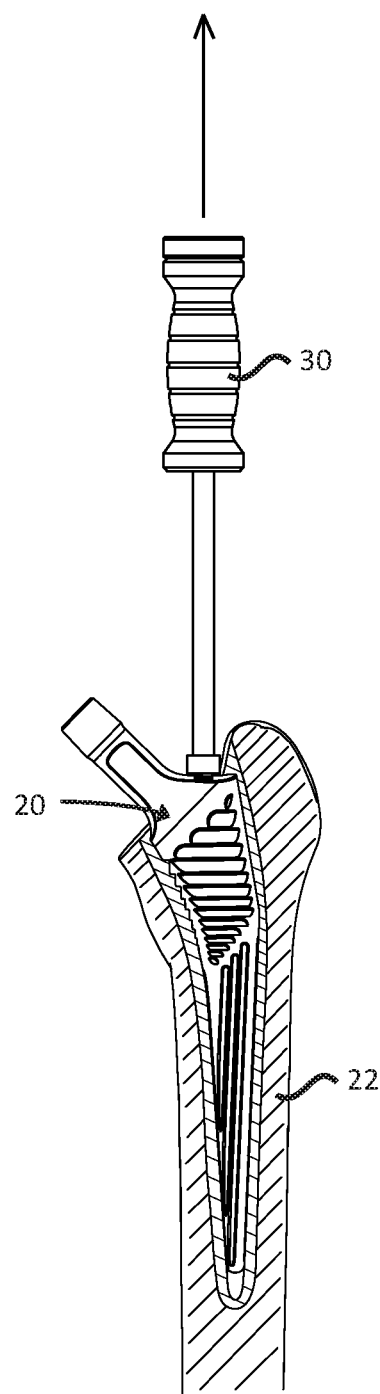
FIG. 2 is a cross-sectional view of a human femur, showing the prosthesis of FIG. 1 and instrumentation (e.g. a slide hammer) for its removal.
Figure 3:
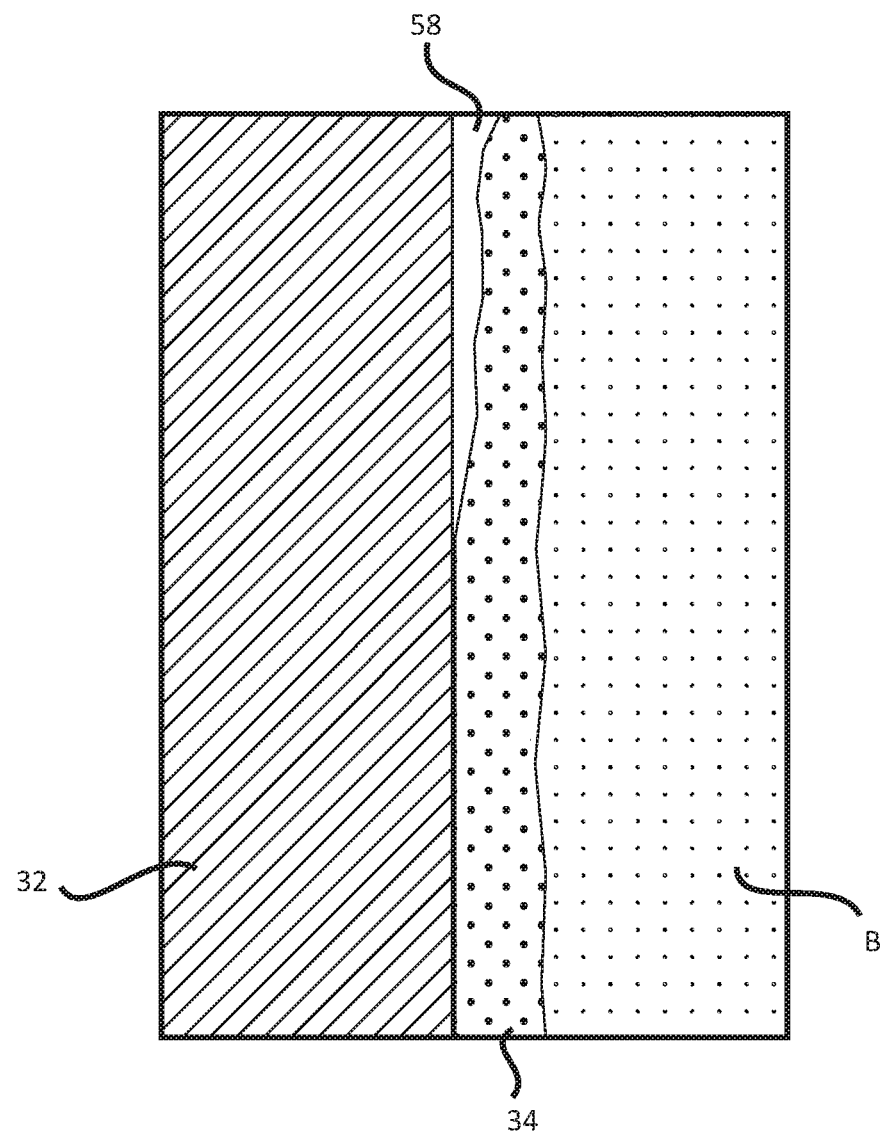
FIG. 3 is a schematic, cross-sectional view of a bond interface between an implant and a bone, illustrating a metal-to-cement-to-bone interface.

FIG. 3 is an enlarged view showing a metal-to-cement-to-bone bond interface between an implant (represented generically at 32) and a bone B. The implant 32, typically made of titanium or another biocompatible alloy, has a smooth external surface facing the bone B. A layer of polymeric bone cement 34 bonds the surface to the bone B.

Figure 4:
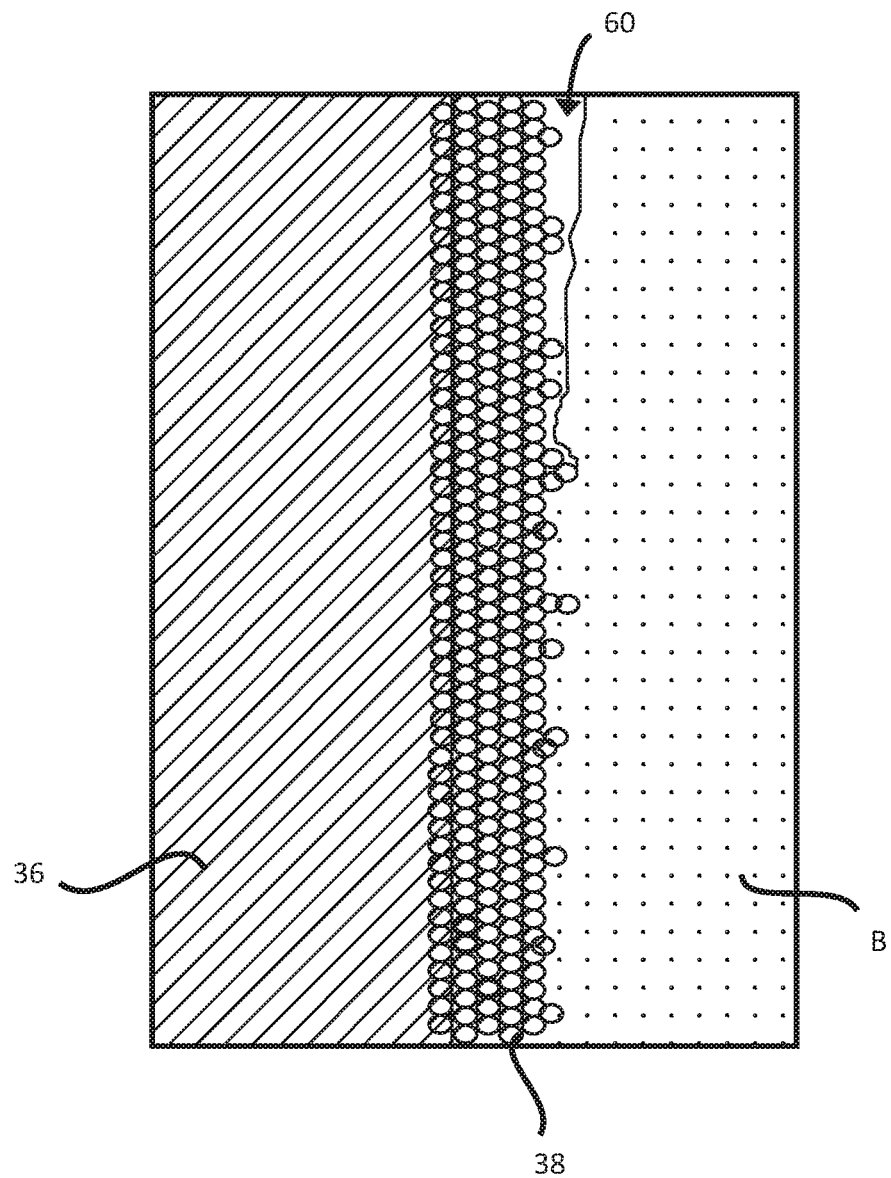
FIG. 4 is a schematic, cross-sectional view of a bond interface between an implant and a bone, illustrating a metal-to-bone interface.

FIG. 4 is an enlarged view showing a metal-to-bone bond interface between an implant 36 and a bone B. The implant 36, typically made of titanium or another biocompatible alloy, has an external osseointegration structure 38 with a surface texture having a controlled degree of roughness. For example a layer of sintered metal or trabecular metal may be applied to the metal surface of the implant 36. After implantation, bone growth infiltrates into the osseointegration structure 38. Alternatively, the osseointegration structure 38 may comprise an oxide layer (naturally occurring or artificially produced). This type of oxidation layer is known to promote bond integration, especially when the implant comprises a titanium alloy.

Figure 5:
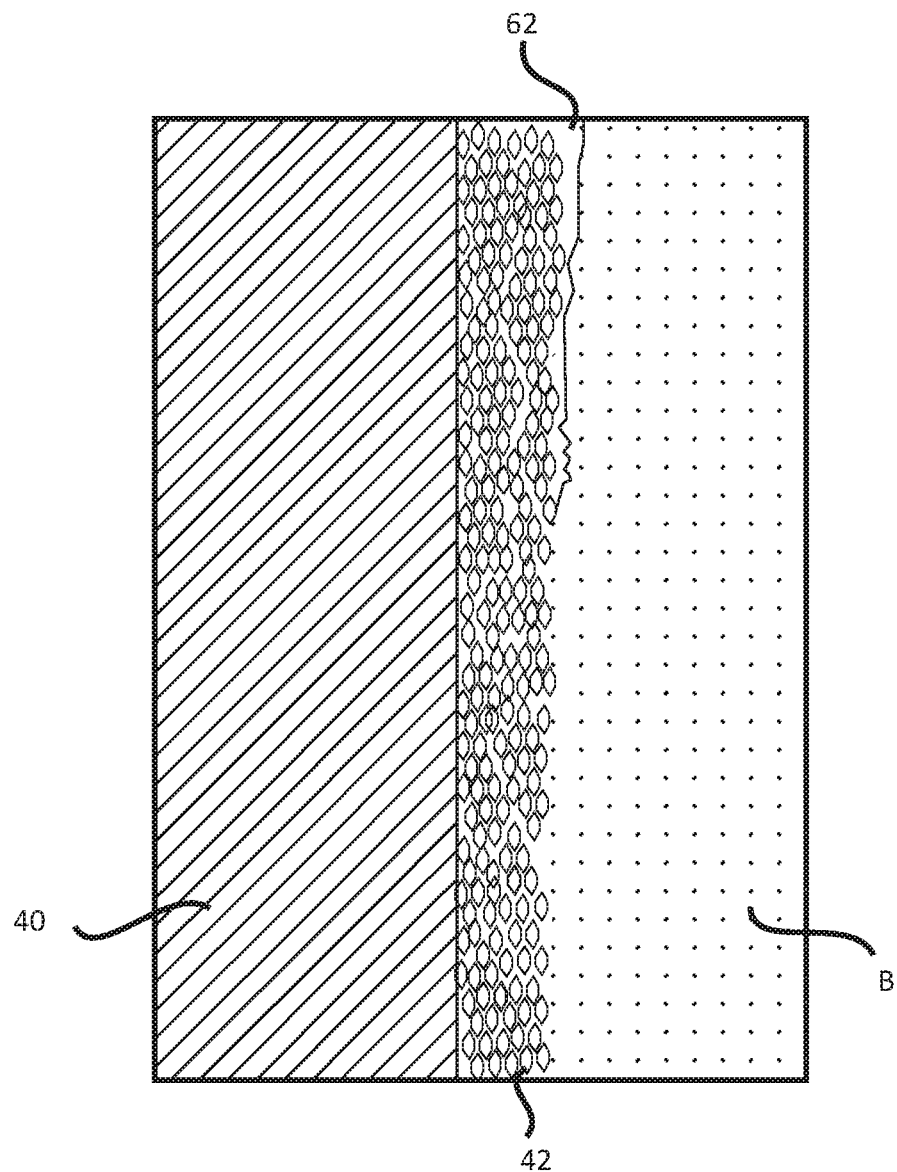
FIG. 5 is a schematic, cross-sectional view of a bond interface between an implant and a bone, illustrating a metal-to-coating-to-bone interface.

FIG. 5 is an enlarged view of a metal-to-coating-to-bond interface between an implant 40 and a bone B. The implant 40, typically made of titanium or another biocompatible alloy, has an external surface. A coating 42 comprising an inorganic crystalline structure such as hydroxyapatite ("HA") is applied to the external surface prior to implantation. After implantation, bone growth infiltrates into the HA coating 42.

In general the method can include vibrational excitation of an implant at or near to one or more of its natural frequencies. The method can further include using multiple frequencies at or near its natural frequencies, and/or multiple vibration vectors in order to input at least a minimum surface energy concentration into a select or targeted area of the bond interface, which may include a significant proportion of the bond interface.

Figure 6:
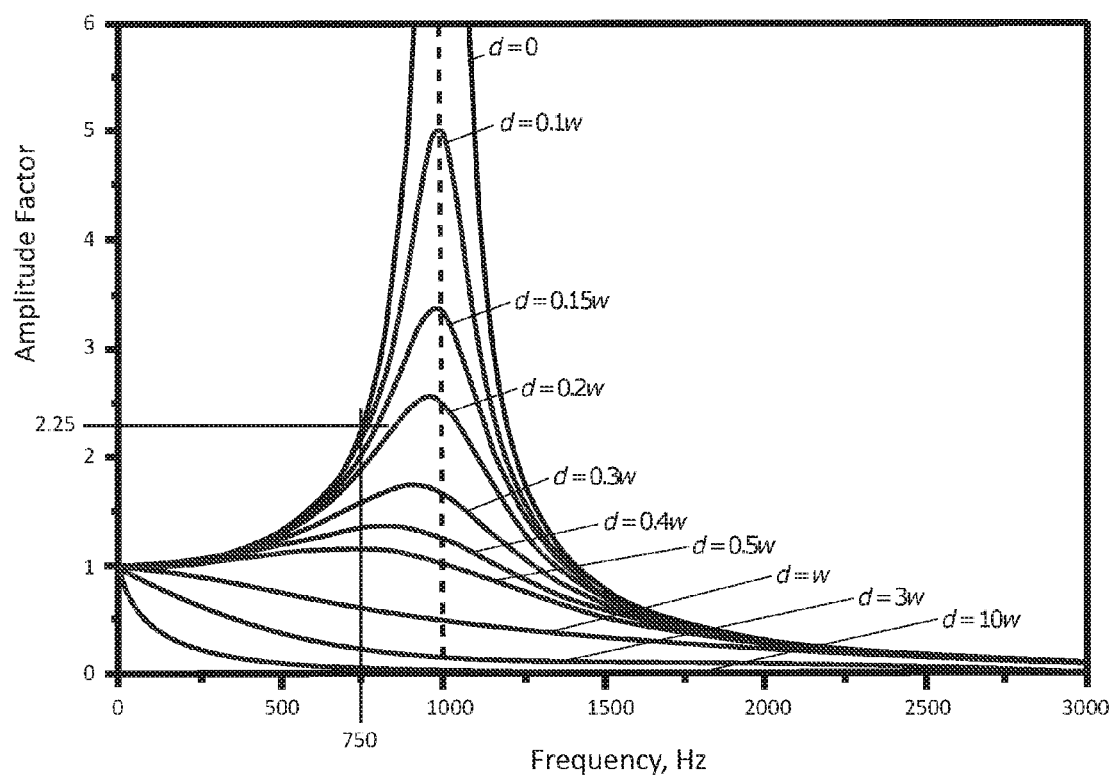
FIG. 6 is a graph illustrating a generalized response of a mechanical element to an applied cyclic excitation force, at various damping coefficients.

FIG. 6 illustrates a generalized response of a mechanical element to an applied cyclic excitation force, with a nondimensional displacement amplitude factor plotted against the excitation frequency. Each curve represents the response for a specific damping coefficient "d". It is well known that every physical object has multiple natural frequencies unique to that object. When excited at or near a natural frequency, the structure's displacement is greater that the amplitude of the excitation displacement. In the example of FIG. 6 the mechanical element is shown as having a first natural frequency of 1000 Hz. When excited at or near this frequency the displacement factor can be several multiples of the input displacement, depending on the damping (if any) present in the system of the object and its surrounding environment. For a given excitation amplitude, a desired amplitude factor can be realized by selecting the specific excitation frequency. For example, in the graph shown in FIG. 6 an excitation frequency of 750 Hz results in a maximum deflection of approximately 2.25 times the excitation amplitude, for the undamped condition.

The mechanical element has a characteristic deflected shape or "mode shape" associated with each natural frequency. FIGS. 7-10 show a simple cantilevered beam 46 having fixed and free ends 48 and 50, respectively, and extending along a neutral axis 52. The beam 46 is modeled as a spring-mass-damper system, and in FIGS. 7-10 the beam 46 is excited at its first, second, third, and fourth natural frequencies, respectively. In this example the forcing function is a simple steady-state oscillating transverse force, applied perpendicular to the neutral axis 52. It should be understood that each of FIGS. 7-10 is a "snapshot" in time, and that the illustrated mode shape would be mirrored about the neutral axis 52 at the following half-cycle.

At the first natural frequency F1, the mode shape includes a single upwards curve or positive deflection, with maximum deflection at the free end of the beam 46.

At the second natural frequency F2, the mode shape includes a significant downwards or negative deflection at the axial locations from approximately 25%-90% of the distance from the fixed end 48 to the free end 50, and an opposite, upwards or positive deflection at the approximate 90%-100% locations.

At the third natural frequency F3, the mode shape includes a significant upwards or positive deflection at approximately the 25%-50% axial locations, an opposite downwards or negative deflection at approximately the 50%-90% locations, and another upwards or positive deflection at approximately the 90%-100% locations.

At the fourth natural frequency F4, the mode shape includes a significant downwards or negative deflection at approximately the 25%-40% axial locations, an upwards or positive deflection at approximately the 40%-60% locations, a downwards or negative deflection at approximately the 60%-90% locations, and another upwards or positive deflection at approximately the 90%-100% locations.

Figure 11:
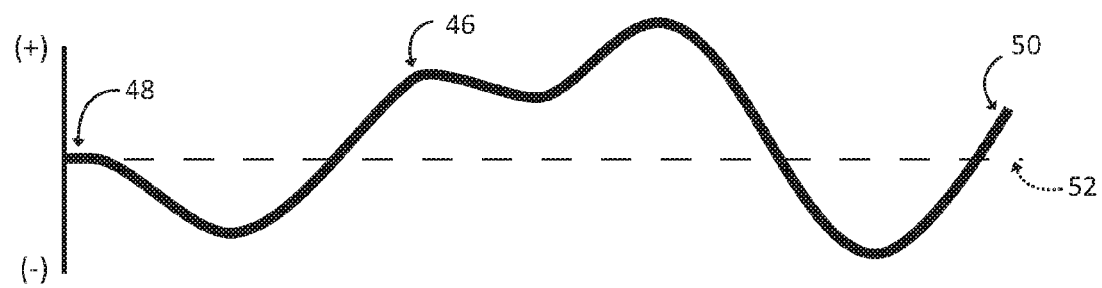
FIG. 11 is a graph illustrating first through fourth mode shapes of a generalized cantilevered beam in response to cyclic excitation forces applied at multiple frequencies.
Figure 12:
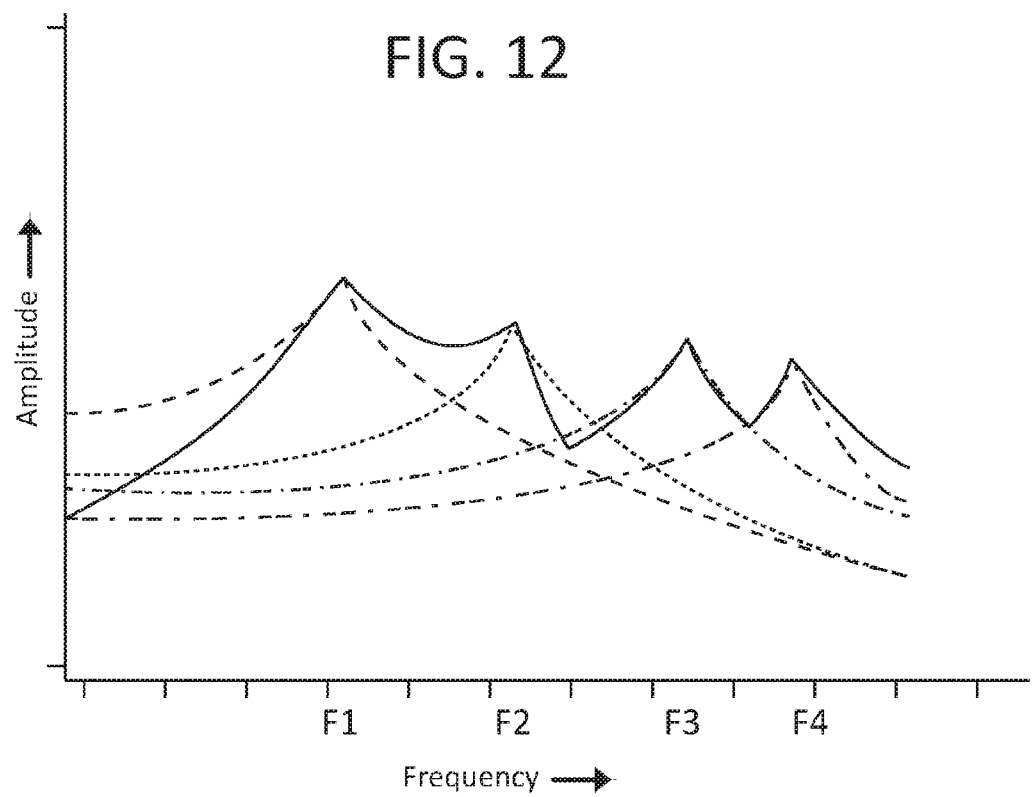
FIG. 12 is a graph illustrating the amplitude response of a generalized cantilevered beam in response to cyclic excitation forces applied at each of four natural frequencies.

Finally, FIG. 11 illustrates the beam 46 with all four frequencies applied simultaneously, and the four mode shapes superimposed together, and FIG. 12 illustrates the amplitude response of the beam 46 at each natural frequency.

According to the principles of the present invention, the harmonic characteristics of the implant can be used to break the bond interfaces described above, efficiently and without causing damage to the bone or excessive trauma.

Figure 13:
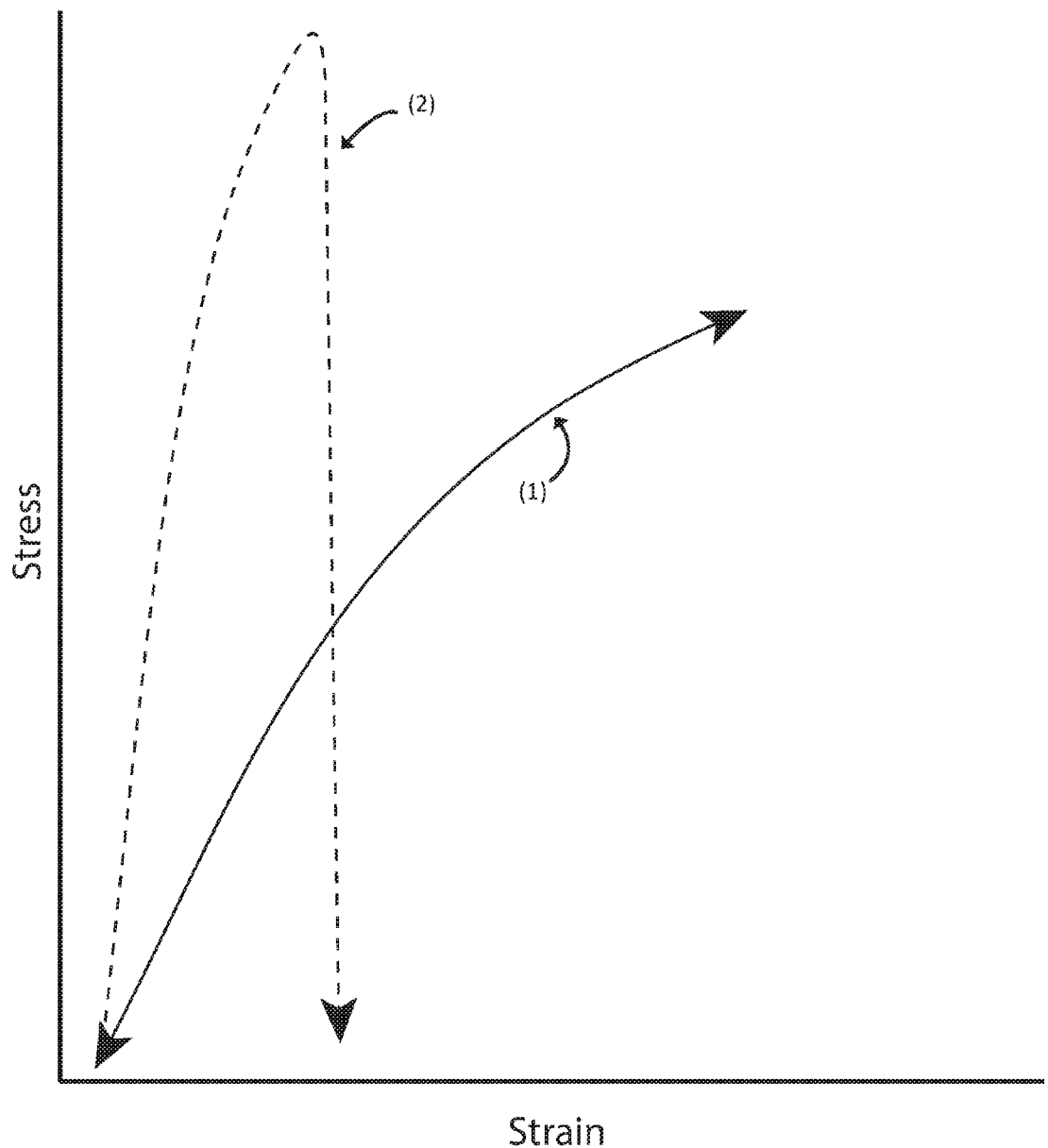
FIG. 13 is a graph illustrating the stress-strain characteristics of bone compared to a bond interface.
Figure 14:
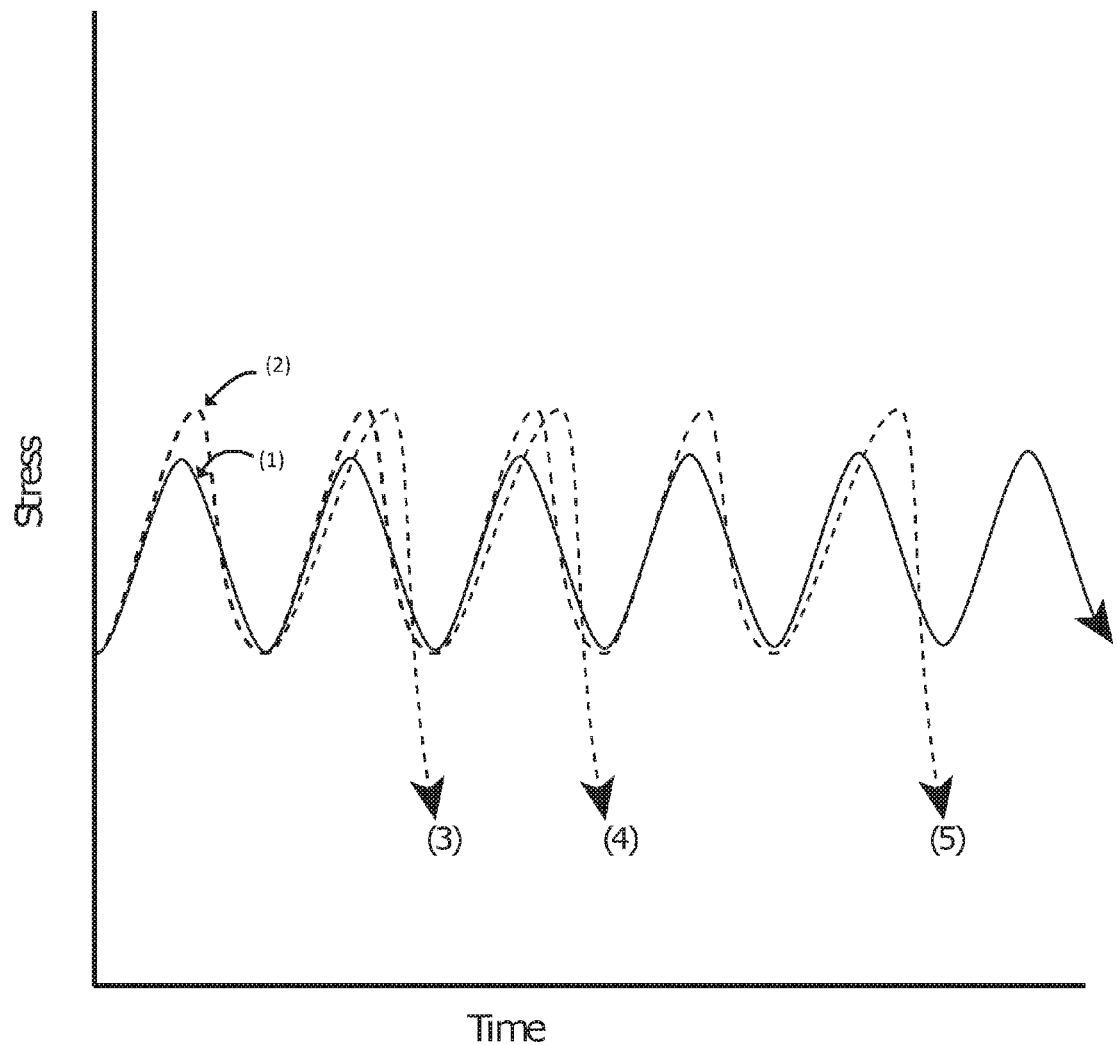
FIG. 14 is a graph illustrating the stress-strain characteristics of bone compared to a bond interface under a cyclic applied force.

FIG. 13 illustrates the stress-strain characteristics of bone, curve (1), compared to the bond interfaces described above. It can be seen that bone has generally ductile properties and has a significant region of elastic deflection. In contrast, the bond interfaces, curve (2) generally have brittle properties with small elongation to failure (curve 2). Accordingly, the bone can survive repeated cyclic deflections, while each cycle breaks more and more of the bond interface. FIG. 14 shows this characteristic, where curve (1) for the bone is able to maintain elasticity over many cycles, while curve (2) for the bond interface suffers brittle fractures at different locations over repetitive cycles, curves (3)(4)(5).

Figure 15:
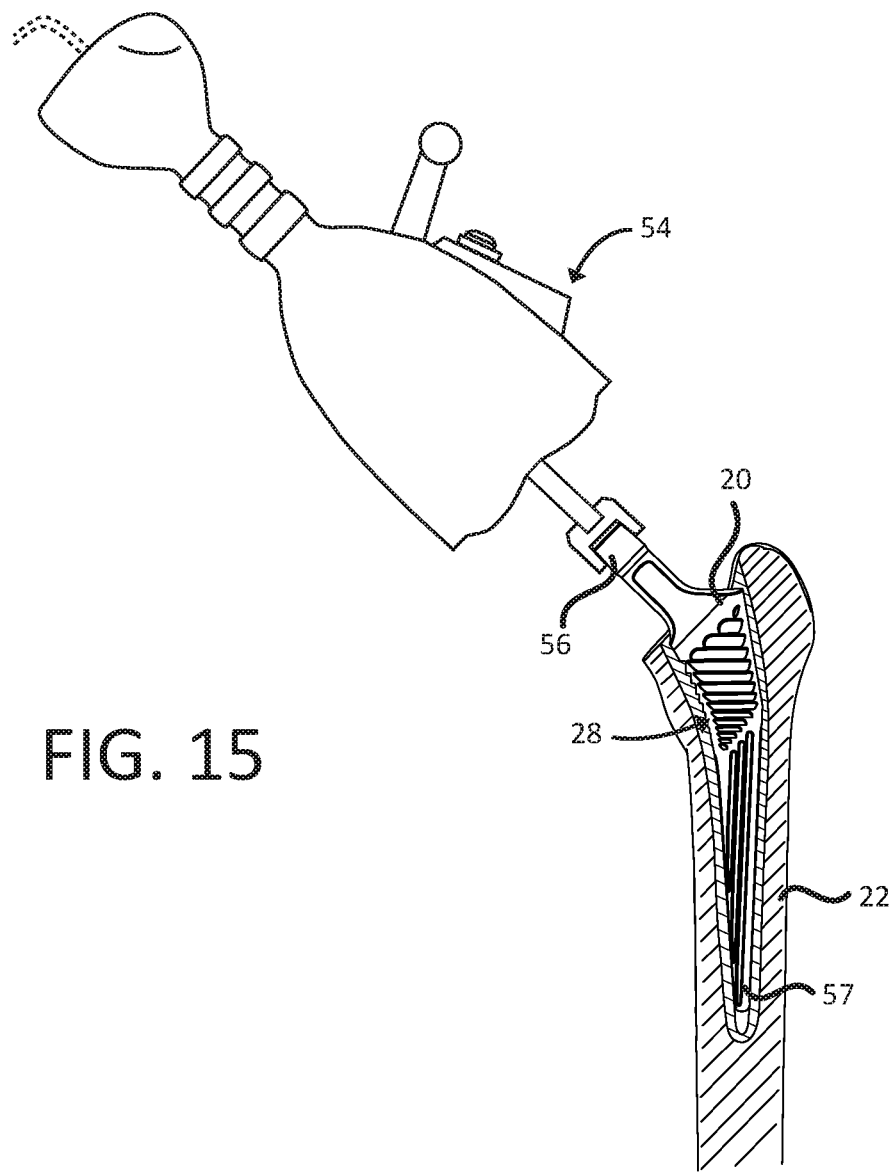
FIG. 15 is a side view of an extractor coupled to a stem-type implant.

The method of applying these principles for extract implantation will now be described in more detail with reference to a stem 20, shown in FIG. 15. An extractor 54, which will be described in more detail below, is coupled to the proximate end 56 of the stem 20 ("proximate" and "proximal" are treated as synonyms herein). The extractor 54 then applies an excitation function (a cyclic excitation force) with a known amplitude, frequency, and vector to the proximate end 56. The cyclic excitation force can be fully described by a parameter set including the amplitude, frequency, vector, and time. Application of this excitation function results in the stem 20 vibrating and transferring surface energy to the bond interface 28 over the entire stem 20, including at the distal end 57. When the surface energy concentration (expressed as value in Jim') exceeds a threshold level, it causes failure of the bond interface 28. It is possible to create specific zones of excitation and therefore break bonds in select areas of the implant either serially or in parallel.

The specific failure mechanism will vary depending on the type of bond interface. For example, in the metal-to-cement-to-bone bond interface in FIG. 3, it is thought that failure (shown at 58) will likely occur between the implant 32 and the cement 34. For the metal-to-bone bond interface in FIG. 4, it is thought that failure (shown at 60) will likely occur between the implant 36 and the osseointegration surface 38. For the metal-to-coating-to-bone bond interface in FIG. 5, it is thought that failure (shown at 62) will likely occur between the coating 42 and the bone B. Failure may be tensile or shear in nature. The exact failure mechanism or location is not critical to the present invention.

Methods of removing implants using ultrasonic vibrations are disclosed in the prior art. In general "ultrasonic" refers to frequencies above the upper limit of human hearing, or approximately 20,000 cycles per second (20 kHz). Use of such frequencies in implant extraction tools results in conversion of a substantial amount of mechanical energy to heat. This is inefficient and may damage surrounding bone. In contrast, the present invention may utilize frequencies well below the ultrasonic threshold in order to efficiently and effectively remove medical implants.

Placing the excitation function at a frequency near or at a natural frequency allows the extraction process to take advantage of an amplitude factor greater than unity. For example, considering the model shown in FIG. 6 as a general representation of the stem 20, a lateral deflection of 0.4 mm (0.015 in.) could be achieved in the distal end 57 of the stem 20 by applying an excitation function at 750 Hz with a deflection of only 0.17 mm (0.007 in.) at the proximate end 56 (i.e. amplitude factor of 2.25). The deflection of the stem 20 can thus be varied for a given input deflection by varying the frequency of the excitation function.

Placing the excitation function at a frequency near or at a natural frequency also allows the surface energy concentration (Jim') to be maximized at the bond interface by taking advantage the various mode shapes. Because in each mode shape the maximum deflection occurs over less than the entire surface area of the stem 20, the surface area where the peak force is applied is decreased and the surface energy concentration is increased for a given input energy.

Figures 16, 17:
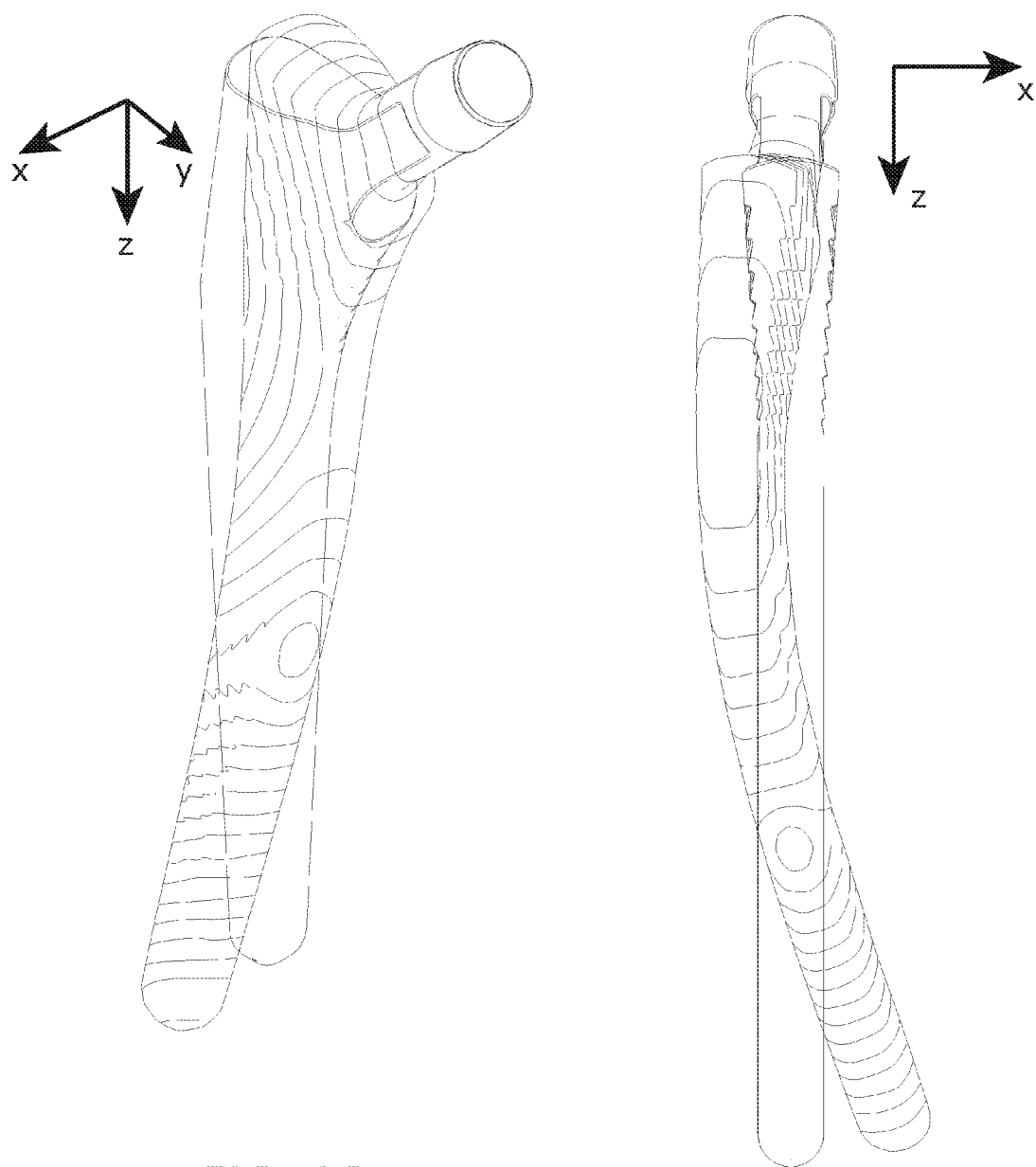
FIG. 16 is an isometric view of an implant stem vibrating in a second mode shape with force applied normal to a Y-Z plane.
FIG. 17 is a rear view of an implant stem vibrating in a second mode shape with force applied normal to a Y-Z plane.
Figure 39:
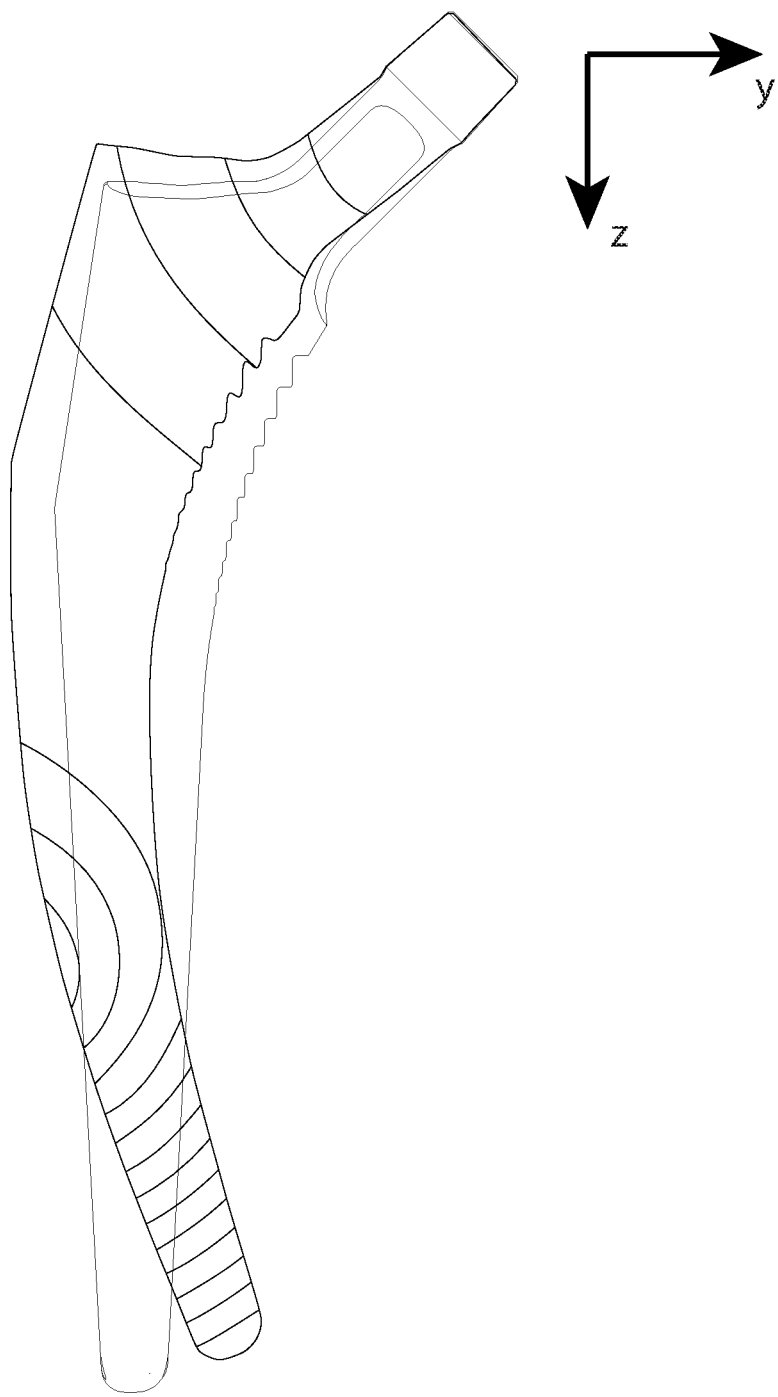
FIG. 39 is a side view of the stem vibrating in a third mode shape with the force applied normal to an X-Z plane.

In order to permit easy extraction of the stem 20, it is helpful to break all or a large portion of the bond interface 28 by sequentially breaking it at different locations on the surface. For example, FIG. 16 and FIG. 17 shows the stem 20 being vibrated at or near a second natural frequency (second mode shape), with the excitation force being applied normal to the Y-Z plane. The maximum deflection occurs, and maximum surface energy concentration would be transferred to the bond interface 28, at the distal end 57. FIG. 39 shows the stem 20 being vibrated at or near a third natural frequency (third mode shape), with the excitation force being applied normal to the X-Z plane.

The bond breakage pattern (location and orientation) may also be enhanced by changing the vector of the excitation function, the term "vector" being used herein to refer to both the alignment and velocity of the applied cyclic force. For example, the function may be translational, applied in any orientation relative to the stem 20, or could be torsional, applied in any orientation relative to the stem 20. For example, the excitation functions in FIGS. 16 and 39 are applied with two different vectors.

Figure 18:
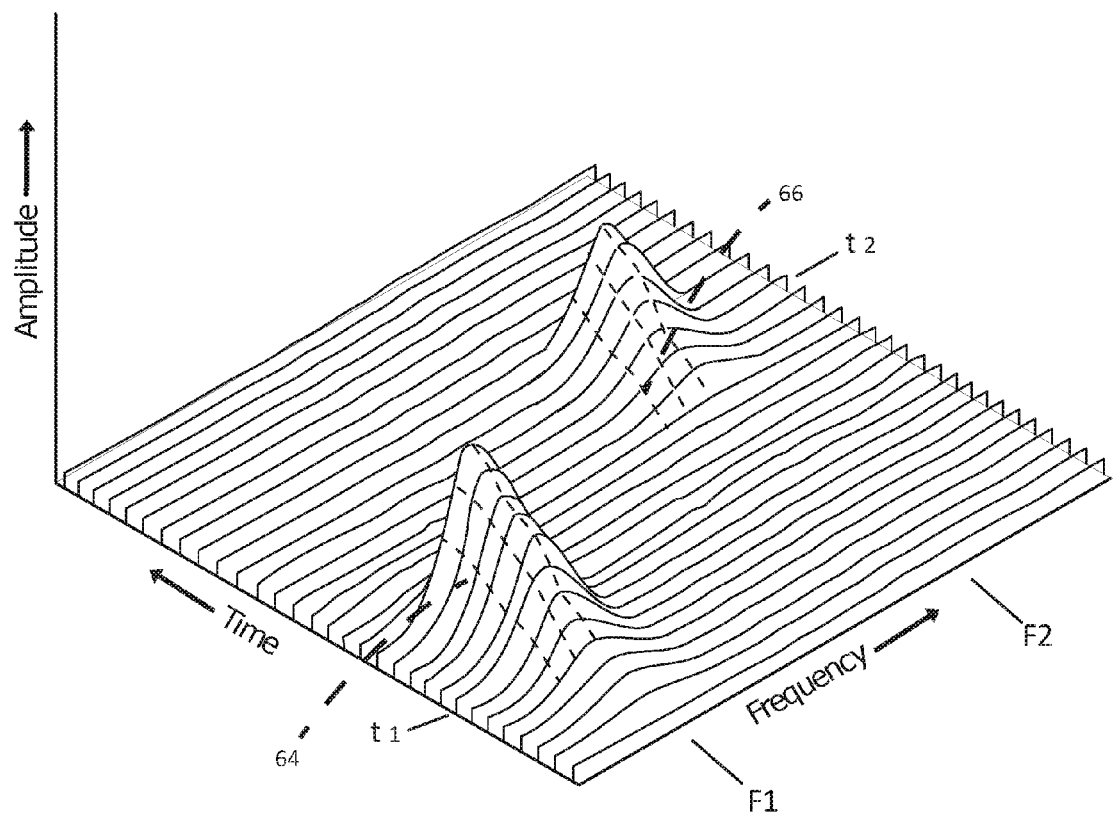
FIG. 18 is a waterfall plot showing a sequence of excitation functions being applied to an implant.

Any number of cyclic excitation forces may be applied in sequence to achieve breakage of all or a large portion of the bond interface. In use, a vibration pattern for a particular implant could include a sequence of excitation forces, with each force specified by vibration parameters including vector, frequency, magnitude (e.g. amplitude or force), and duration. For example, FIG. 18 is a waterfall plot showing the amplitude response of an implant vs. frequency and time. In this example, a first excitation function, shown by dashed line 64, is applied at first time T1, at a frequency near a first natural frequency F1. Subsequently, a second excitation function, shown by dashed line 66, is applied at second time T2, at a frequency near a second natural frequency F2. The excitation function can be tailored to achieve the desired implant motion. It is also possible to monitor the frequency response and terminate excitation once a threshold of vibration has been reached. Once breakage of an adequate portion of the bond interface has occurred, it is possible that the stem 20 may be removed using only moderate force. As used herein, the term "moderate" refers to forces significantly less that used in prior art implant removal tools which depend solely on mechanical force or impact. For example, a standard prior art slide hammer having a 1 kg mass can be used to generate peak forces of about 10 kN (2200 lb.) and scores of hammer blows would typically be required. In contrast, the present invention the moderate removal force to extract the stem 20 may be on the order of a single slide hammer blow with a peak force of around 1 kN (200 lb.).

Figure 19:
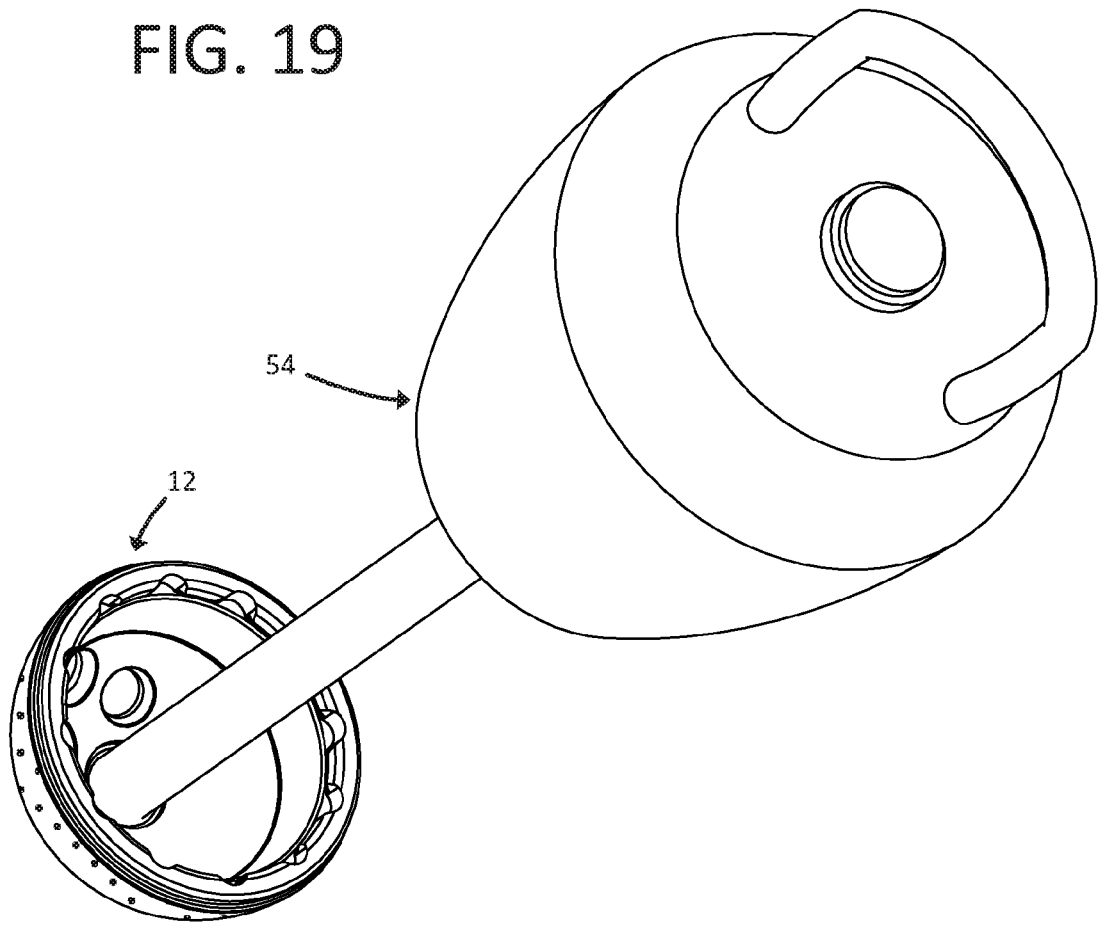
FIG. 19 is a isometric view of an extractor coupled to a cup-type bone implant
Figures 20, 21:
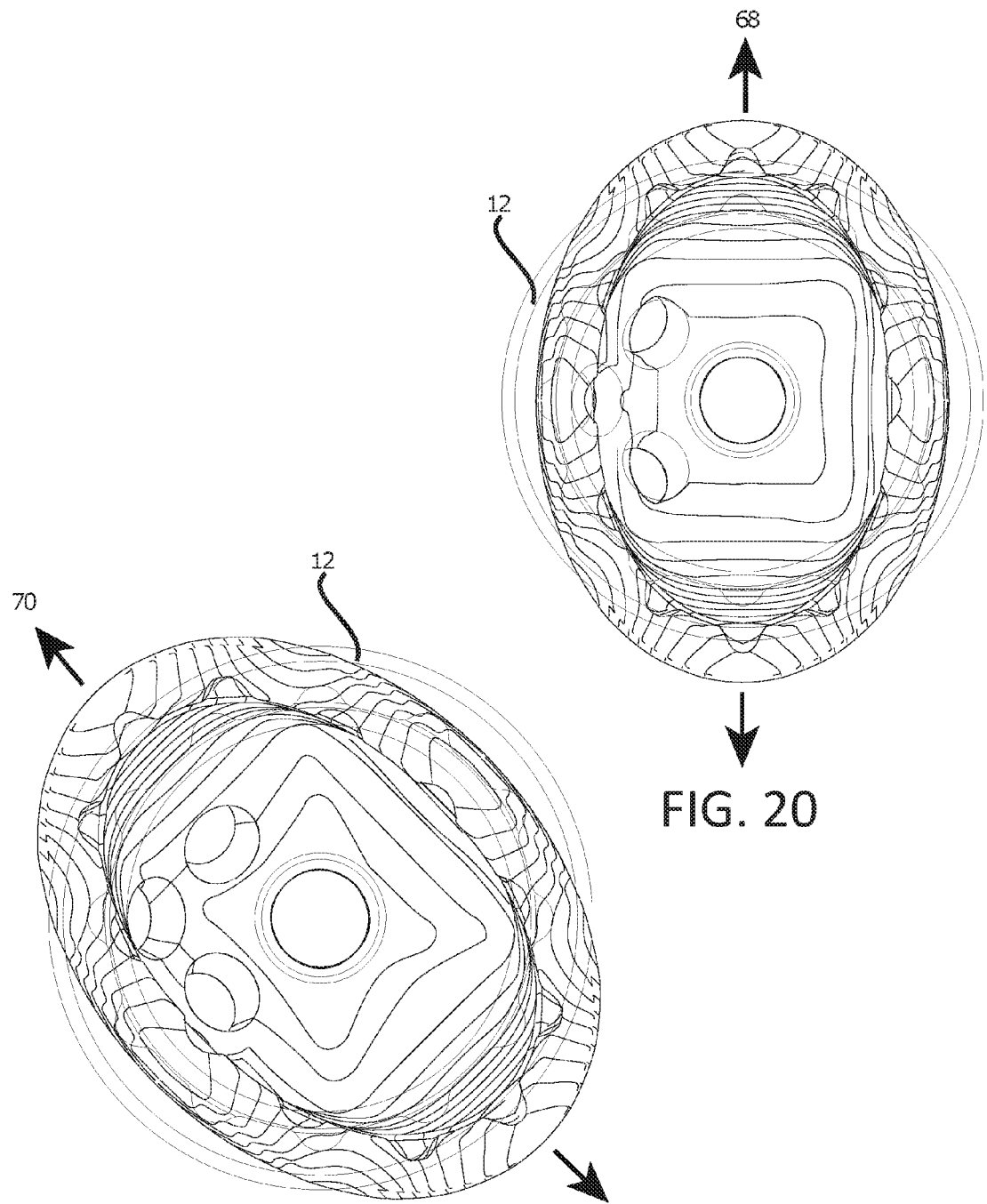
FIG. 20 is a top view of an implant cup vibrating in a third mode shape.
FIG. 21 is a top view of an implant cup vibrating in a forth mode shape.

As another example, FIG. 19 shows an extractor 54 coupled to an acetabular cup 12. As with the stem 20, the cup 12 can be easily extracted by breaking all or a large portion of the bond interface by sequentially breaking it at different locations on the surface. For example, FIG. 20 shows the cup 12 being vibrated at or near a third natural frequency (third mode shape), The maximum deflection occurs, and maximum surface energy concentration would be transferred to the bond interface, along a first axis 68. FIG. 20 shows the cup 12 being vibrated at or near a forth natural frequency (forth mode shape). The maximum deflection occurs, and maximum surface energy would be transferred to the bond interface, along a second axis 70.

The excitation functions described above may be applied in various ways. One possible method of extraction would be manual operation, by connecting an extractor to an implant and then manually selecting one or more of the vibration parameters (e.g. vector, frequency, magnitude, and duration). The remaining vibration parameters could be fixed or pre-set.

Another possible method of extraction would be automated or semi-automated operation, by connecting an extractor to an implant and then automatically applying a vibration pattern comprising several different functions. For example the extractor 54 could be programmed to vibrate the implant at several different frequencies in sequence, with a constant or changing vibration vector.

As another possible option, a custom vibration pattern could be predetermined. The user would connect the extractor 54 to the implant and then start operation. The extractor 54 would apply the sequence of excitation forces according to the custom vibration pattern. The vibration pattern could be selected to cover the surface of the implant with a specific surface energy concentration using the fewest number of functions.

An appropriate custom vibration pattern may be determined by analysis, e.g. by software modeling, or empirically by vibrating a representative implant in a laboratory environment and measuring the response.

Any of the processes described above may be enhanced by the use of feedback. In the implanted condition, the implant is significantly damped by surrounding bone. When the excitation function is initially applied, the damped displacement (as measured at the coupling between the extractor and the implant) will be much less than undamped displacement. As the bond interface starts to break and damping is reduced, a step increase in displacement will occur. Detection of this step increase can be used as an indicator signal that the implant is ready for a subsequent excitation function or for removal.

Figure 22:
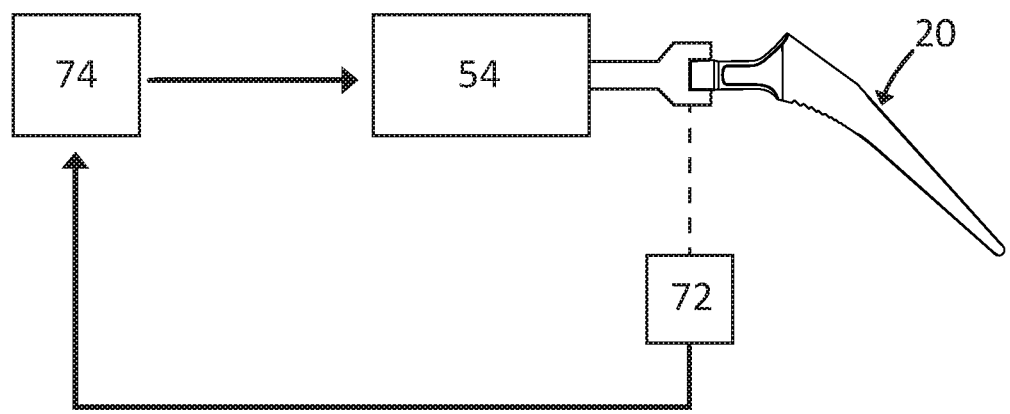
FIG. 22 is block diagram showing an extractor and an implant connected in a control feedback loop.

It is also possible to test the condition of the implant by using the extractor to apply a small-scale excitation function to the implant and measuring the response. FIG. 22 is a block diagram showing the extractor 54 coupled to a stem 20, with a sensor 72 used to measure the implant's response (e.g. displacement, velocity, and/or acceleration) and send a signal to a controller 74. The controller 74 may be programmed to control the extractor based on the feedback signal from the sensor 72.

Figure 23:
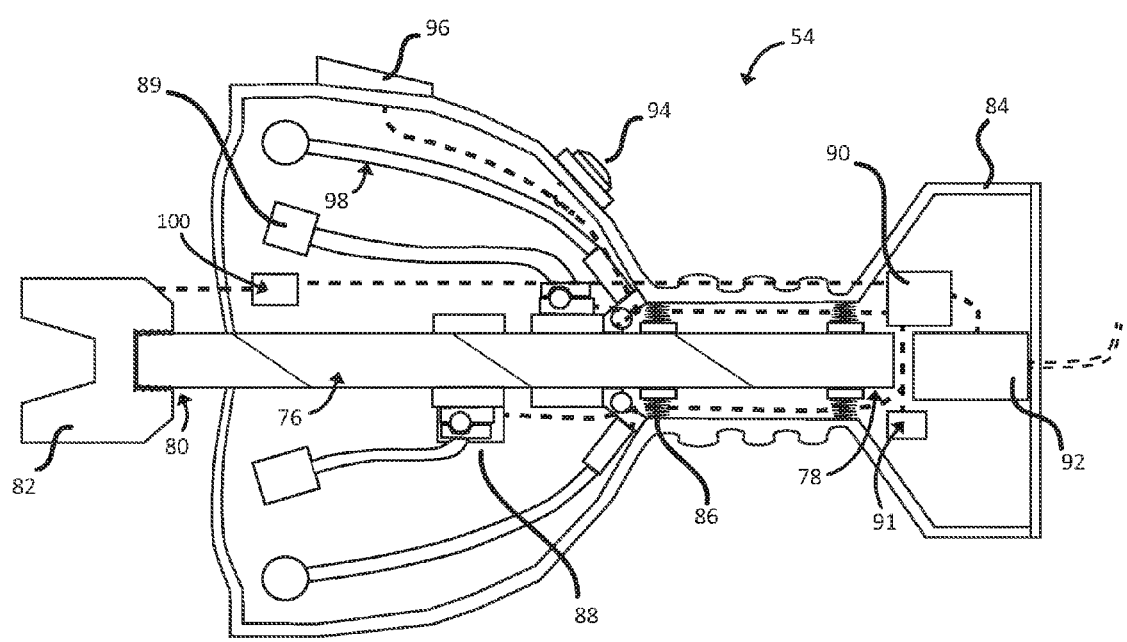
FIG. 23 is a schematic cross-sectional diagram of an exemplary extractor.

FIG. 23 illustrates an exemplary extractor 54 useful for carrying out the method of the present invention in more detail. The extractor 54 includes a shaft 76 with proximate and distal ends 78, 80. The distal end 80 accepts a coupler 82 and the proximate end 78 is mounted in a housing 84 such that it can oscillate relative to the housing 84, for example using the illustrated damping springs 86. A forcing mechanism 88 is coupled to the shaft 76 and is operable to oscillate the shaft 76 according to desired vibration parameters (e.g. frequency, magnitude, and vector) as discussed above. The forcing mechanism 78 may be any apparatus operable to oscillate the shaft 76 in a controllable manner and may produce, for example, an oscillation which is rotary, lateral, axial, orbital, or combinations thereof. The extractor 54 also includes appropriate elements needed to operate the forcing mechanism 88. In the illustrated example the extractor 54 includes an electronic controller 90 which is connected to the forcing mechanism 88, an electrical power supply 92, user controls 94, and an information display 96, and a remote communications module 91 (e.g. BLUETOOTH, Wi-Fi, or other wireless communication protocol). The transceiver permits remote communications with a local or remote device (e.g. computer workstation, mobile computing device, or purpose-built communications device). This remote communications capability may be used to review data produced by the extractor 54 and/or to send information or commands to the extractor 54. For example, a surgeon or other user could remotely review sensor data from the extractor 54 and subsequently create or choose a vibration plan and transmit the vibration plan to the extractor 54 for use in performing an extraction.

Optionally, the extractor 54 may include a damping mechanism 98 operable to damp the vibration transmitted to the housing 84. For example, the damping mechanism 98 may comprise a second forcing mechanism operating out-of-phase with the forcing mechanism.

The extractor 54 may include one or more sensors 100 for providing vibration feedback to the controller 92 from the operation. For example the sensor 100 may measure displacement, velocity, and/or acceleration of the coupler 82.

The forcing mechanism 88 may be any device operable to oscillate the shaft 76 according to desired vibration parameters (e.g. frequency, magnitude, and vector). FIGS. 24-27 illustrate examples of possible forcing mechanisms.

Figure 24:
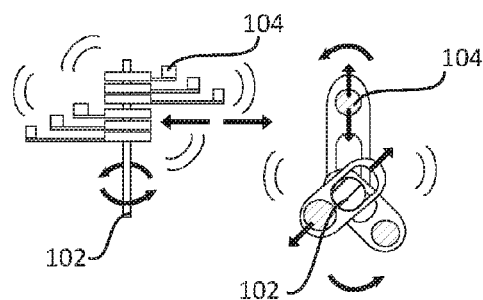
FIG. 24 is a schematic view of a forcing mechanism.
Figure 40:
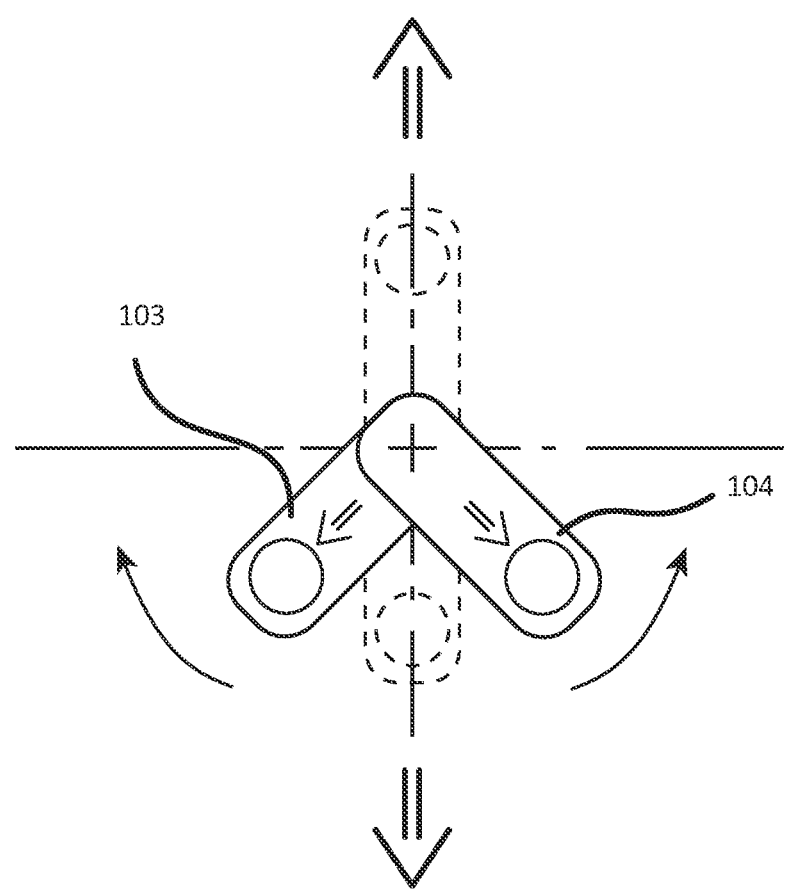
FIG. 40 is a schematic end view of a forcing mechanism

For example, FIG. 24 illustrates a rotatable shaft 102 carrying counterweights 104. The counterweights 104 are positioned in an unbalanced configuration relative to the shaft 102 and may be moveable to change their distance from the shaft 102. This type of mechanism inherently changes the excitation vector as it operates. It is possible to also have a second set of independent counterweights 103 (see FIG. 40) that can operate in coordination with weights 104 to create a desired excitation frequency, magnitude, and vector. For example weight set 104 may rotate in one angular direction denoted as the plus direction and the second set 103 may be programmed to operate in the minus rotational direction, thus causing a combined centrifugal forcing vector that may only excite in a directed cyclical excitation vector with no (canceled) lateral motion. Therefore, it is possible to create a magnitude, frequency, and angular vector directed excitation force with minimal lateral centrifugal (whirling) component if desired.

Figure 25:
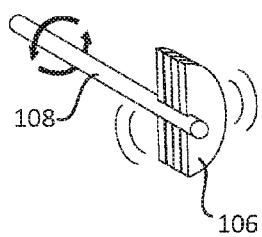
FIG. 25 is a schematic view of a forcing mechanism.

FIG. 25 illustrates a stationary mass 106 attached to an oscillating shaft 108.

Figure 26:
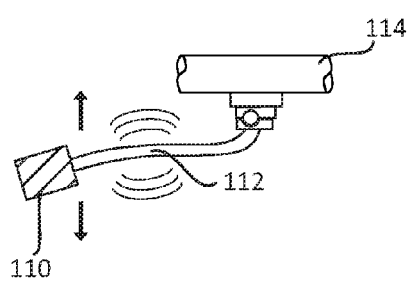
FIG. 26 is a schematic view of a forcing mechanism.

FIG. 26 illustrates a mass 110 attached to an arm 112 which is rotatable about a shaft 114. Rotation of the mass 110 about the shaft 112 (for example using an electric motor, not shown) generates an excitation force. Similar to the mechanism shown in FIG. 24, the excitation vector inherently changes as the mechanism operates. It is possible to also have a second independent arm with a rotating mass that can operate in coordination with weight 110 to create a desired excitation frequency, magnitude, and vector. For example weight 110 may rotate in one angular direction denoted as the plus direction and the second set may be programmed to operate in the minus rotational direction, thus causing a combined centrifugal forcing vector that may only excite in a directed cyclical excitation vector with minimal lateral loading (canceled forces—lateral to the desired forcing function vector). Therefore, it is possible to create a magnitude, frequency, and angular vector directed excitation force with no lateral centrifugal (whirling) component if desired. In this construct the effect can be enhanced by the native geometry of a mass on a beam that is also able to deflect along with the excitation force thus presenting the opportunity for a very efficient (peak aggregate excitation force versus overall total mass and energy expended) excitation mechanism by coordinating both the rotation and the mass deflection on the arm to generate a desired forcing function.

Figure 27:
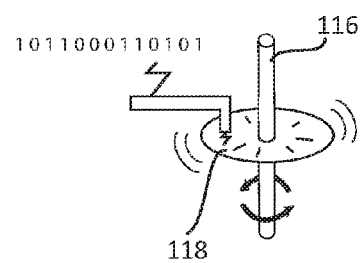
FIG. 27 is a schematic view of a forcing mechanism.

FIG. 27 illustrates a shaft 116 having a magnetic braking motor 118 attached thereto. Operation of the motor 118 causes a torsional vibration in the shaft 116. This method would be particularly useful when a torsional excitation forcing function is desired.

Figure 28:
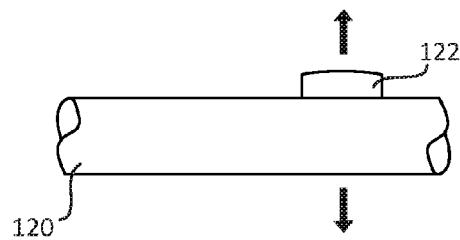
FIG. 28 is a schematic view of a forcing mechanism.

FIG. 28 illustrates a shaft 120 having an electromechanical vibrator 122 attached thereto. The vibrator 122 is effective to produce a transverse vibration in one plane. The vibrator 122 may be rotated relative to the shaft 120 to change the vector of the vibration.

It should also be noted that it is possible to mount an excitation device similar to vibrator 122, or other forcing function generator and apply a load on any vector over the aft hemisphere of the stem. (i.e. "polar" coordinate loading variable at any of the three positional angular of degrees of freedom).

Operation of the extractor 54 is most efficient when there is a solid mechanical connection between the implant and the extractor 54, without lost motion. The connection should also be capable of being readily connected and disconnected. FIGS. 29-33 illustrate various possible configurations for the coupler 82 shown in FIG. 23.

FIG. 29 illustrates a coupler 82 having a recess 124 formed therein. The recess 124 is frustoconical in shape, with a perimeter surface 126 and an end surface 128. The dimensions of the perimeter surface 126 (e.g. diameter "D" and taper angle THETA) are selected to provide a desired amount of interference with the proximate end 56 of the stem 20. The coupler 82 may be installed and removed manually or with tools, depending on the degree of interference. The coupler is one or more components and may be press fit or manually clamped. A taper extraction means may be provided to eject the stem taper after extraction.

FIG. 30 illustrates another coupler 130 having a recess 132 formed therein. The recess 132 is frustoconical in shape, with a perimeter surface 134 and an end surface 136. An annular pressure chamber 138 surrounds the recess 132 and is separated from the recess by a relatively thin dividing wall 140. A port 142 is provided communicating with the pressure chamber 138. The dimensions of the perimeter surface 134 (e.g. diameter "D" and taper angle THETA) may be selected to accept the proximate end 56 of the stem 20 with minimal force. Subsequently, fluid under pressure can be introduced into the pressure chamber 138 through the port 142, causing the dividing wall 140 to flex and apply clamping pressure to the proximate end 56, retaining it securely. Venting the pressurized fluid from the pressure chamber 138 permits the dividing wall 140 to spring back and release the clamping pressure.

FIG. 31 illustrates another coupler 144 having a recess 146 formed therein. The recess 146 is frustoconical in shape, with a perimeter surface 148 and an end surface 150. The dimensions of the perimeter surface 148 (e.g. diameter "D" and taper angle THETA) may be selected to accept the distal end 56 of the stem 20 with minimal force. A locking element 152 in the form of a collar, spring arms, or similar structure surrounds the recess 146 and presents a flange 154 (continuous or segmented) that bears against the distal end 56. In use, the flange 154 is driven axially against the distal end 56, retaining it securely in the recess 146. The locking element 152 can be backed off or removed in order to disconnect the stem 20.

FIG. 32 illustrates another coupler 156 having a recess 158 formed therein. The recess 158 is frustoconical in shape, with a perimeter surface 160 and an end surface 162. A heating device 164 such as an electrical resistance heater surrounds the recess 158. The dimensions of the perimeter surface 160 (e.g. diameter "D" and taper angle THETA) may be selected to provide a desired amount of interference with the distal end 56 of the stem 20. To insert or remove the stem 20, the heating device 164 would be used to heat and expand the recess 158 (shown greatly exaggerated in FIG. 33). To clamp the stem 20 in place, the heating device 164 would be turned off to allow the coupler 156 to cool and shrink over the stem 20 (see FIG. 32).

Figure 34:
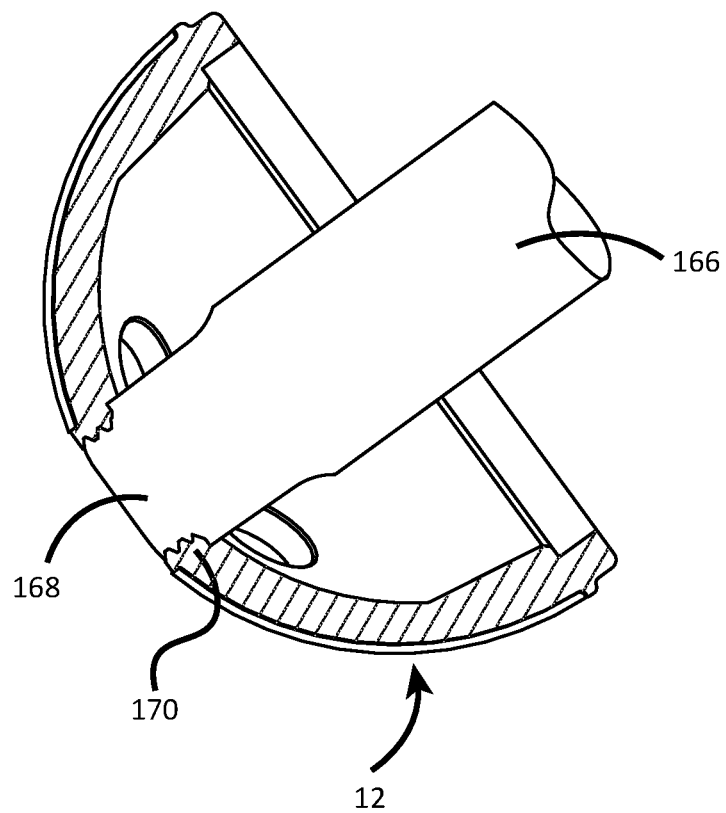
FIG. 34 is a schematic, cross-sectional view of a coupler.

FIG. 34 illustrates another coupler 166 comprising a simple threaded portion 168. Implants are frequently provided with threaded holes to facilitate attachment of installation tools. This type of coupler 166 can be easily attached to those holes. For example, FIG. 34 shows the coupler 166 attached to a threaded hole 170 in an acetabular cup 12.

Figures 37, 38:
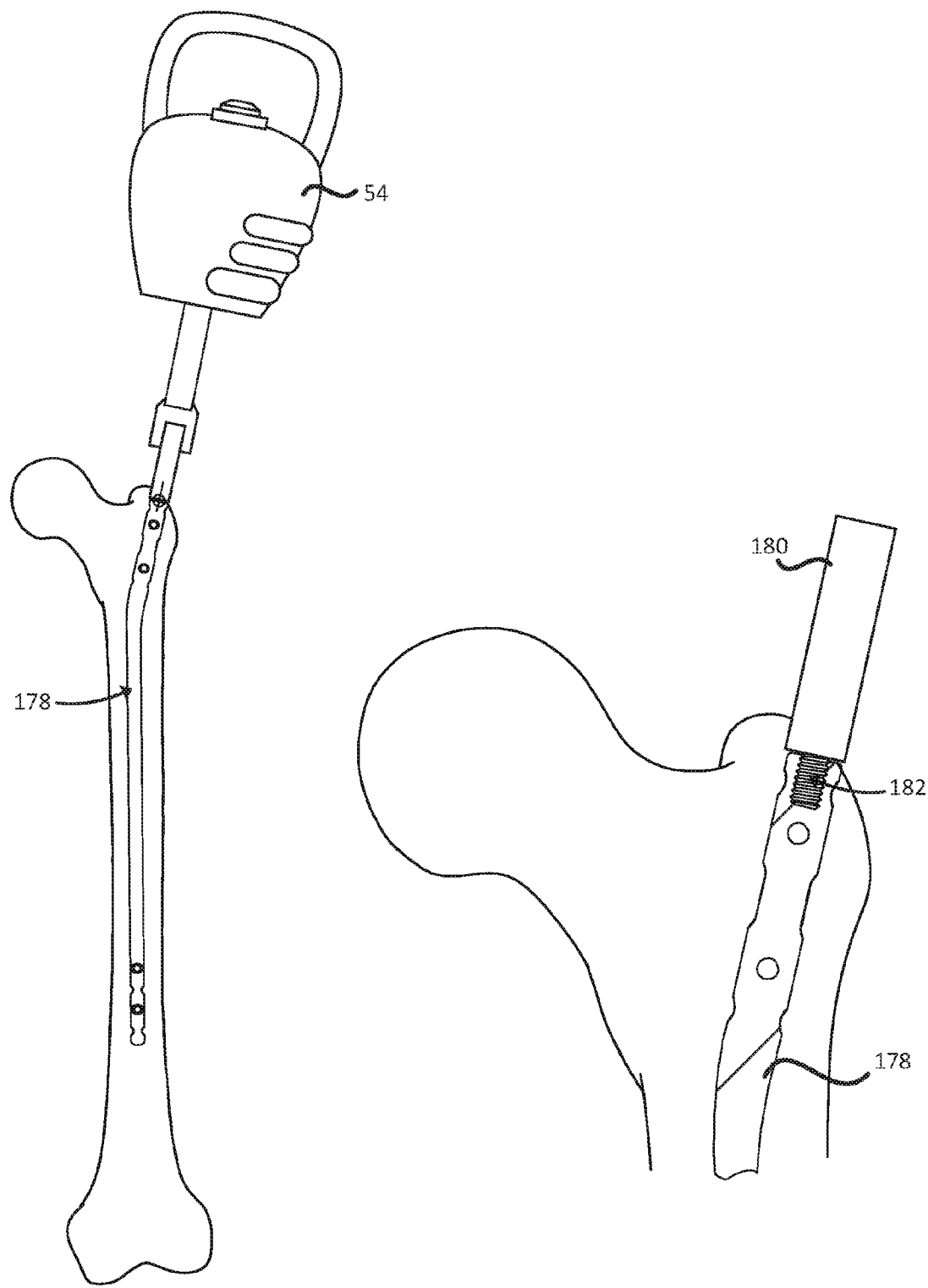
FIG. 37 is a view of an intramedullary rod with an extractor device attached.
FIG. 38 is a close up view of the extractor and intramedullary rod of FIG. 37, showing attachment via a threaded rod.

As another example, FIG. 37 shows an intramedullary rod 178 implanted in a femur, with an extractor 54 coupled thereto. FIG. 38 shows a coupler 180 used to connect the extractor 54 to the intramedullary rod 178, comprising a simple threaded portion 182.

Figure 35:
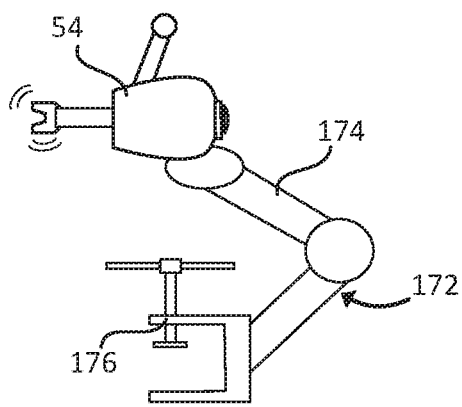
FIG. 35 is a schematic side view of an extractor connected to a mount.

In use the extractor 54 may hand-held or may be mounted to a table or other suitable support, for example using a mount 172 having articulated arms 174 and a clamp 176, seen in FIG. 35.

Figure 36:
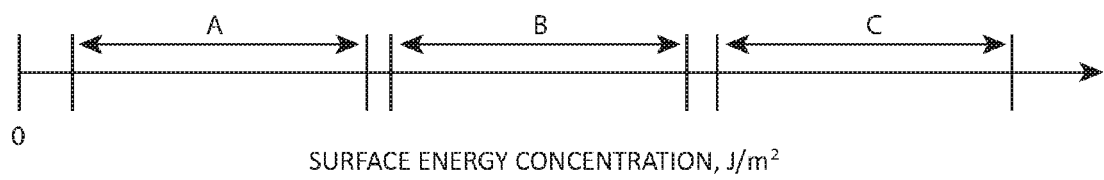
FIG. 36 is a schematic scale showing ranges of surface energy concentration.

In addition to the extraction methods described above, the apparatus and methods describe herein can also be used for implantation and/or fusion of implants. FIG. 36 is a scale depicting surface energy applied to a bone/implant interface, where the implant is coated with HA as described above. At high surface energy concentrations, zone "C", crystal bonds are broken and extraction can take place. It is a known property of HA that, in a lower range of surface energy concentration, zone "A", the vibration causes bonds to form. Thus, operation of the extractor 54 at these lower surface energy concentrations can cause instantaneous fusion of the implant to bone. In a third zone "B" intermediate to zones A and C, the surface energy concentration is too great to create crystal bonds and too little to break them. Operation of the extractor 54 in this zone can be used to overcome static friction and efficiently drive an implant into a bone cavity with minimal trauma and low overall forces. It is also possible to operate the extractor 54 at these lower surface energy concentrations post-implantation to stimulate both growth.

The apparatus and method described herein has numerous benefits compared to the prior art. A primary benefit is a large reduction in the time required to remove an implant. For example, removal of an implanted stem 20 can often take 90 minutes using existing techniques. Analysis has shown that the method described herein has the potential to reduce that time by 75% or more. Another significant benefit is a large reduction in trauma to bone and the surrounding tissues. The method described herein has the ability to break the bond interface with small amplitude vibrations that do not damage the surrounding bone, and may even enhance bone density. Breaking the bond interface will permit the implant to be extracted using only minimal force, with no impact forces. Furthermore, extraction can occur with a straight line pulling force, avoiding bending forces on the bone. This combination of time and trauma reduction will result in faster healing, improved outcomes, and significant cost savings to the surgeon, hospital, and patient.

The foregoing has described apparatus and methods for extraction of medical implants. All of the features disclosed in this specification, and/or all of the steps of any method or process so disclosed, may be combined in any combination, except combinations where at least some of such features and/or steps are mutually exclusive.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends, or to any novel one, or any novel combination, of the steps of any method or process so disclosed.

What is claimed is:

1. A method for removing a medical implant embedded in a bone at a bond interface, wherein the bond interface is metal-to-bone, metal-to-cement-to bone, metal-to-oxidation layer-to-bone, or metal-to-coating-to-bone, the method comprising:
   mechanically connecting a coupler of an extractor that includes a forcing mechanism connected to the coupler and to an electronic controller to an exposed portion of the medical implant;
   using the extractor to apply a series of cyclic excitation forces to the exposed portion of the medical implant, wherein each cyclic excitation force is described by a parameter set including a specified amplitude, frequency, vector, and duration, wherein the parameter set of each cyclic excitation force is unique, such that the medical implant vibrates and transfers surface energy to the bond interface, causing failure of the bond interface at a plurality of different locations, wherein a frequency of each of the cyclic excitation forces is near or at a natural frequency of the medical implant, such that a ratio of deflection of the medical implant at the bond interface to a deflection of the medical implant at the exposed portion is greater than unity.

2. The method of claim 1 wherein the frequency of each of the cyclic excitation forces is below the ultrasonic range.

3. The method of claim 1 further comprising pulling the medical implant away from the bone after failure of the bond interface, using only moderate force.

4. The method of claim 1 wherein the cyclic excitation forces are applied such that failure of the bond interface is caused at different locations sequentially.

5. The method of claim 1 wherein the cyclic excitation forces are applied such that failure of the bond interface is caused at different locations concurrently.

6. The method of claim 1 further comprising applying a cyclic excitation force at two or more different frequencies in sequence.

7. The method of claim 1 further comprising applying a cyclic excitation force including at least two different frequencies concurrently.

8. The method of claim 1 further comprising:
   using a vibration sensor coupled to the coupler to provide a vibration feedback signal representative of vibration of the coupler; and
   using the electronic controller, controlling at least one aspect of the cyclic excitation force in response to the vibration feedback signal.

9. The method of claim 8 wherein the step of controlling the cyclic excitation force includes:
   measuring a displacement at the coupler while applying the cyclic excitation force; and
   in response to detection of a step increase in the measured displacement, generating an indicator signal.

10. The method of claim 9 further comprising, in response to the indicator signal, using the electronic controller to change at least one of the frequency, amplitude, and vector of the cyclic excitation force.

11. The method of claim 9 further comprising, in response to the indicator signal, using the electronic controller to stop the cyclic excitation force.

12. The method of claim 1 wherein each of the parameter sets is predetermined before beginning the extraction method.

13. The method of claim 1 further comprising:
   prior to applying the series of cyclic excitation forces, applying a small-scale excitation force insufficient to cause failure of the bond interface to the medical implant;
   using a vibration sensor coupled to the coupler to provide a vibration feedback signal representative of vibration of the coupler; and
   determining at least one aspect of the series of cyclic excitation forces in response to the vibration feedback signal.

* * * * *